United States Patent
Lu et al.

(10) Patent No.: US 10,949,811 B2
(45) Date of Patent: Mar. 16, 2021

(54) HEALTH CONDITION MONITORING AND ACTION

(71) Applicant: International Business Machines Corporation, Armonk, NY (US)

(72) Inventors: Fang Lu, Billerica, MA (US); Joseph Lam, Markham (CA); Trudy L. Hewitt, Cary, NC (US); William K. Wentworth, Round Rock, TX (US)

(73) Assignee: International Business Machines Corporation, Armonk, NY (US)

( * ) Notice: Subject to any disclaimer, the term of this patent is extended or adjusted under 35 U.S.C. 154(b) by 216 days.

(21) Appl. No.: 15/855,093

(22) Filed: Dec. 27, 2017

(65) Prior Publication Data

US 2019/0156296 A1    May 23, 2019

Related U.S. Application Data

(63) Continuation of application No. 15/821,031, filed on Nov. 22, 2017.

(51) Int. Cl.
*G06Q 10/00* (2012.01)
*G06Q 50/00* (2012.01)
(Continued)

(52) U.S. Cl.
CPC ......... *G06Q 10/1095* (2013.01); *A61B 5/024* (2013.01); *A61B 5/1118* (2013.01);
(Continued)

(58) Field of Classification Search
CPC .................. G06Q 10/00–50/00; A61B 5/00
(Continued)

(56) References Cited

U.S. PATENT DOCUMENTS 8,185,426 B1 *  5/2012  Khoubyari ..... G06Q 10/063116
                                                     705/7.19
8,328,643 B1 * 12/2012  Osvald .................. G06Q 10/101
                                                      463/42
(Continued)

OTHER PUBLICATIONS

List of IBM Patents or Patent Applications Treated as Related, Jan. 31, 2018, 2 pages.
(Continued)

*Primary Examiner* — Eric W Stamber
*Assistant Examiner* — Mustafa Iqbal
(74) *Attorney, Agent, or Firm* — Heslin Rothenberg Farley & Mesiti P.C.; Scott Dobson, Esq.

(57) ABSTRACT

A method, computer program product, and system includes a processor(s) continuously monitoring a current condition of a user of an Internet of Things (IoT) device, via the IoT device. The processor(s) determines that the current condition indicates an issue with the well-being of the user. The processor(s) identifies upcoming event(s), within a given temporal period, in which the user will participate. The processor(s) determines that the current condition of the user will negatively impact at least one event of the upcoming event(s). The processor(s) generates action(s) comprising a change to the event, where the action(s) is executed by interacting with one or more applications deployed on the one or more target computer resources (accessible to the one or more processors via a network connection). The processor(s) automatically executes the at least one action on the one or more target computer resources.

6 Claims, 5 Drawing Sheets

(51) Int. Cl.
*A61B 5/00* (2006.01)
*G06Q 10/10* (2012.01)
*A61B 5/024* (2006.01)
*A61B 5/11* (2006.01)
*A61B 5/16* (2006.01)

(52) U.S. Cl.
CPC .............. *A61B 5/165* (2013.01); *A61B 5/168* (2013.01); *A61B 5/4815* (2013.01); *G06Q 10/1097* (2013.01); *G06Q 50/01* (2013.01)

(58) Field of Classification Search
USPC ................................................ 705/7.11–7.42
See application file for complete search history.

(56) References Cited

U.S. PATENT DOCUMENTS

| | | | |
|---|---|---|---|
| 8,781,568 | B2 | 7/2014 | Dugan et al. |
| 2015/0012342 | A1* | 1/2015 | Rostamian ......... G06Q 30/0252 705/14.5 |
| 2015/0320359 | A1 | 11/2015 | Luo |
| 2016/0066827 | A1 | 3/2016 | Workman et al. |
| 2016/0192874 | A1 | 7/2016 | Canavan et al. |
| 2016/0199008 | A1 | 7/2016 | Lyon et al. |
| 2016/0223578 | A1* | 8/2016 | Klosinski, Jr. ......... G01C 21/08 |
| 2016/0300263 | A1* | 10/2016 | Priness .............. G06Q 30/0261 |
| 2017/0039339 | A1* | 2/2017 | Bitran .................... G16H 40/63 |

OTHER PUBLICATIONS

Lu et al., "Health Condition Monitoring and Action," U.S. Appl. No. 15/821,031, filed Nov. 22, 2017, pp. 1-38.

Mell et al., "The NIST Definition of Cloud Computing", National Institute of Standards and Technology, U.S. Dept. of Commerce, NIST Special Publ. 800-145, Sep. 2011, 7 pages.

* cited by examiner

HEALTH CONDITION MONITORING AND ACTION

BACKGROUND

The Internet of Things (IoT) is a system of interrelated computing devices, mechanical and digital machines, objects, animals and/or people that are provided with unique identifiers and the ability to transfer data over a network, without requiring human-to-human or human-to-computer interaction. These communications are enabled by smart sensors, which include, but are not limited to, both active and passive radio-frequency identification (RFID) tags, which utilize electromagnetic fields to identify automatically and to track tags attached to objects and/or associated with objects and people. Smart sensors, such as RFID tags, can track environmental factors related to an object, including but not limited to, temperature and humidity. The smart sensors can be utilized to measure temperature, humidity, vibrations, motion, light, pressure and/or altitude. IoT devices also include individual activity and fitness trackers, which include (wearable) devices or applications that include smart sensors for monitoring and tracking fitness-related metrics such as distance walked or run, calorie consumption, and in some cases heartbeat and quality of sleep and include smartwatches that are synced to a computer or smartphone for long-term data tracking. Because the smart sensors in IoT devices carry unique identifiers, a computing system that communicates with a given sensor can identify the source of the information. Within the IoT, various devices can communicate with each other and can access data from sources available over various communication networks, including the Internet.

Individuals in particularly stressful situations, which result in a low quality of sleep, are occasionally hesitant to request help from others or to make changes to upcoming scheduled events, even if those others are willing to provide the help and the upcoming events can be rescheduled. For example, a parent of a newborn baby may be under a large amount of stress and would likely benefit from assistance, but is unaware of the stress he or she is experiencing and how assistance from another could help rectify certain health issues the parent may be experiencing, based on this unfamiliar predicament. Similarly, an individual who lacks a sufficient amount of sleep or a certain quality of sleep may have difficulty participating in a productive meeting in this compromised state.

SUMMARY

Shortcomings of the prior art are overcome and additional advantages are provided through the provision of a method for generating and executing actions based on data from an Internet of Things (IoT) device. The method includes, for instance: continuously monitoring, by one or more processors, a current condition of a user of an IoT device, via the IoT device; determining, by the one or more processors, that the current condition indicates an issue with the well-being of the user; identifying, by the one or more processors, one or more upcoming events, within a given temporal period, in which the user will participate; determining, by the one or more processors, that the current condition of the user will negatively impact at least one event of the more one or more upcoming events; generating, by the one or more processors, at least one action comprising a change to the at least one event to mitigate the negative impact, wherein the at least one action is executed by interacting with one or more applications deployed on the one or more target computer resources, wherein the one or more target computer resources are accessible to the one or more processors via a network connection; and automatically executing, by the one or more processors, the at least one action on the one or more target computer resources.

Shortcomings of the prior art are overcome and additional advantages are provided through the provision of a computer program product for generating and executing actions based on data from an Internet of Things (IoT) device. The computer program product comprises a storage medium readable by a processing circuit and storing instructions for execution by the processing circuit for performing a method. The method includes, for instance: continuously monitoring, by the one or more processors, a current condition of a user of an IoT device, via the IoT device; determining, by the one or more processors, that the current condition indicates an issue with the well-being of the user; identifying, by the one or more processors, one or more upcoming events, within a given temporal period, in which the user will participate; determining, by the one or more processors, that the current condition of the user will negatively impact at least one event of the more one or more upcoming events; generating, by the one or more processors, at least one action comprising a change to the at least one event to mitigate the negative impact, wherein the at least one action is executed by interacting with one or more applications deployed on the one or more target computer resources, wherein the one or more target computer resources are accessible to the one or more processors via a network connection; and automatically executing, by the one or more processors, the at least one action on the one or more target computer resources.

Methods and systems relating to one or more aspects are also described and claimed herein. Further, services relating to one or more aspects are also described and may be claimed herein.

Additional features are realized through the techniques described herein. Other embodiments and aspects are described in detail herein and are considered a part of the claimed aspects.

BRIEF DESCRIPTION OF THE DRAWINGS

One or more aspects are particularly pointed out and distinctly claimed as examples in the claims at the conclusion of the specification. The foregoing and objects, features, and advantages of one or more aspects are apparent from the following detailed description taken in conjunction with the accompanying drawings in which:

DETAILED DESCRIPTION

The accompanying figures, in which like reference numerals may refer to identical or functionally similar elements throughout the separate views and which are incorporated in and form a part of the specification, further illustrate the present invention and, together with the detailed description of the invention, serve to explain the principles of the present invention. As understood by one of skill in the art, the accompanying figures are provided for ease of understanding and illustrate aspects of certain embodiments of the present invention. The invention is not limited to the embodiments depicted in the figures.

Figure 3:
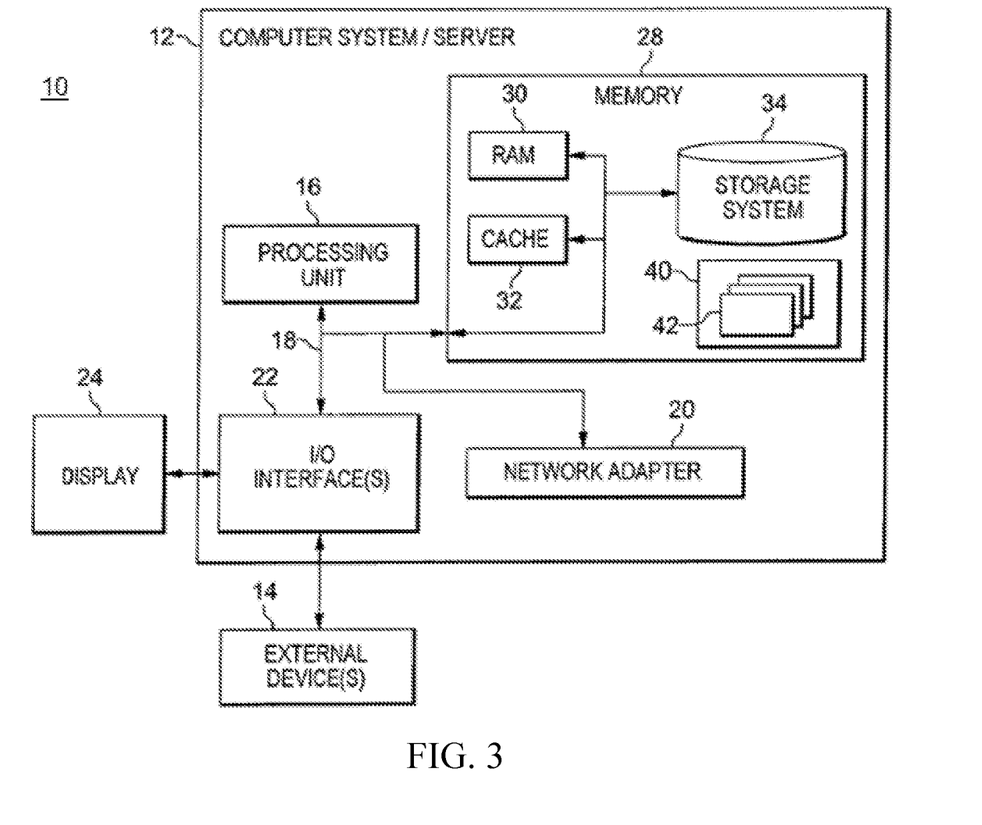
FIG. 3 depicts one embodiment of a computing node that can be utilized in a cloud computing environment.

As understood by one of skill in the art, program code, as referred to throughout this application, includes both software and hardware. For example, program code in certain embodiments of the present invention includes fixed function hardware, while other embodiments utilized a software-based implementation of the functionality described. Certain embodiments combine both types of program code. One example of program code, also referred to as one or more programs, is depicted in FIG. 3 as program/utility 40, having a set (at least one) of program modules 42, may be stored in memory 28.

Embodiments of the present invention include a computer-implemented method, a computer program product, and a computer system that include one or more programs that: 1) monitor a current condition of a user (including health conditions and sleep patterns) via an IoT device proximal to and/or worn by the user, including but not limited to, an activity tracker or smartphone; 2) associates the current condition (e.g., irregular sleep patterns, hypertension, etc.) with upcoming events in which the user will participate that could be impacted by the current condition of the user; 3) determines the impacts of the current condition of the upcoming events; and 4) interacts with various systems accessible by the IoT device over a public and/or private network connection to take actions that mitigate anticipated issues based on the impacts.

The manner and content of the actions taken by the one or more programs may vary. In some embodiments of the present invention, based on determining the impacts of the current condition of the upcoming events, the one or more programs obtain the user's personal data (including contact information) and electronically alerts select individuals to request assistance for the user. In some embodiments of the present invention, the one or more programs interact with various systems that are physically external to the IoT in order to obtain assistance, automatically and/or automatically make changes that would assist the user. In some embodiments of the present invention, the one or more programs take actions in real-time (or close to real-time), based on a health condition, as enabled by the interconnectivity and communications between different computer systems. In embodiments of the present invention, the one or more programs share condition information between systems within trusted network, enabling the temporal functionality of the embodiments without compromising the security and/or privacy of the user of the IoT and/or the security and/or privacy of any users privy to the resultant action(s).

Embodiments of the present invention may be integrated into existing IoT devices to provide an enhancement to some existing functionality. For example, certain existing IoT systems identify a user's heart rate information as related to the user's sleep information, detect a user's sleep apnea issue(s), identify a user's biometric data as it relates to the user's sleep patterns, and/or identify a user's motion data for use in determining if the user got sufficient sleep. Thus, although these existing IoT systems arguably monitor current health conditions of a user, unlike embodiments of the present invention, these existing IoT system do not include one or more programs that associate the current condition with upcoming events in which the user will participate that could be impacted by the current condition of the user, determine the impacts of the current condition of the upcoming events, and interact with various systems accessible by the IoT device over a public and/or private network connection to take actions that mitigate anticipated issues based on the impacts. To give two non-limiting examples, unlike these existing systems, one or more programs in some embodiments of the present invention: 1) notify a trusted party when the user experiences certain sleep issues; and/or 2) adjust a user's upcoming meeting in a shared electronic calendar computing system, based on determinations related to the user's sleep pattern. Thus, existing systems can be utilized with aspects of embodiments of the present invention to provide significantly more functionality than encompassed in those existing systems, alone.

Embodiments of the present invention are inextricably tied to computing and provide advantages over existing activity/health tracking technologies by utilizing IoT devices, such as personal activity trackers, to trigger concrete actions, based on an observed condition of the device user, that mitigate issues identified by the tracker, by utilizing the interconnectivity of computing system accessible to the IoT device. Embodiments of the present invention externalize data formerly available only within an IoT device and to the wearer of the device. Also, one or more programs in embodiments of the present invention interact with computer systems physically external to the IoT device in order to trigger actions within those computing systems. For example, based on one or more programs in an embodiment of the present invention identifying a predetermined health condition of the IoT device user, the one or more program modify one or more upcoming events in a scheduling system and send notifications to one or more additional users impacted by the modification. The temporal advantages of embodiments of the present invention are enabled by the integration of various computing systems and the intercommunication of these systems. Embodiments of the present invention also provide privacy and security to users engaged with various aspects of embodiments of the present invention by utilizing security and privacy measures unique to computing technology.

Figure 1:
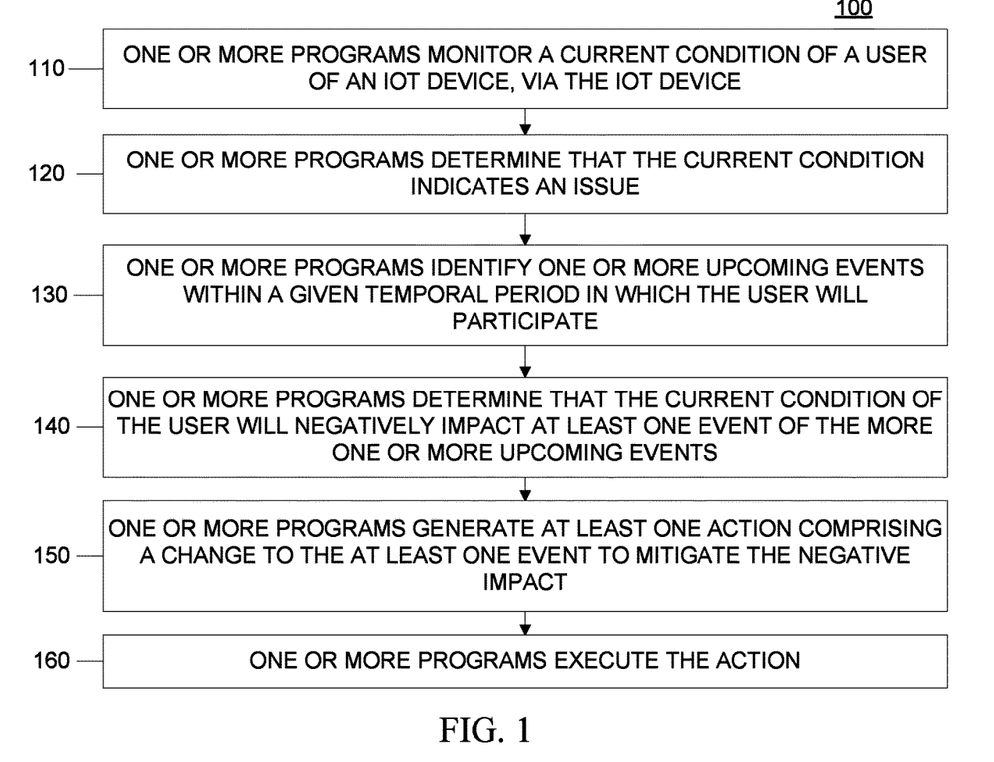
FIG. 1 is a workflow illustrating certain aspects of an embodiment of the present invention.

FIG. 1 is a workflow 100 that illustrates certain aspects of some embodiments of the present invention. FIG. 1 is provided as an overview of certain functionality. These aspects will be reference in FIG. 2, which diagrams an implementation of aspects of some embodiments of the present invention in a technical environment 200. As understood by one of skill in the art, FIGS. 1-2 are provided as non-limiting examples of certain embodiments and implementations in order to better illustrate certain aspects.

Referring to FIG. 1, in an embodiment of the present invention, one or more programs, executed by one or more processors, monitor a current condition of a user of an IoT device, via the IoT device (110). The one or more programs determine that the current condition indicates an issue (120). The one or more programs identify one or more upcoming events within a given temporal period in which the user will participate (130). The one or more programs determine that the current condition of the user will negatively impact at least one event of the more one or more upcoming events (140). The one or more programs generate at least one action comprising a change to the at least one event to mitigate the negative impact (150). The one or more programs execute the action (160).

Figure 2:
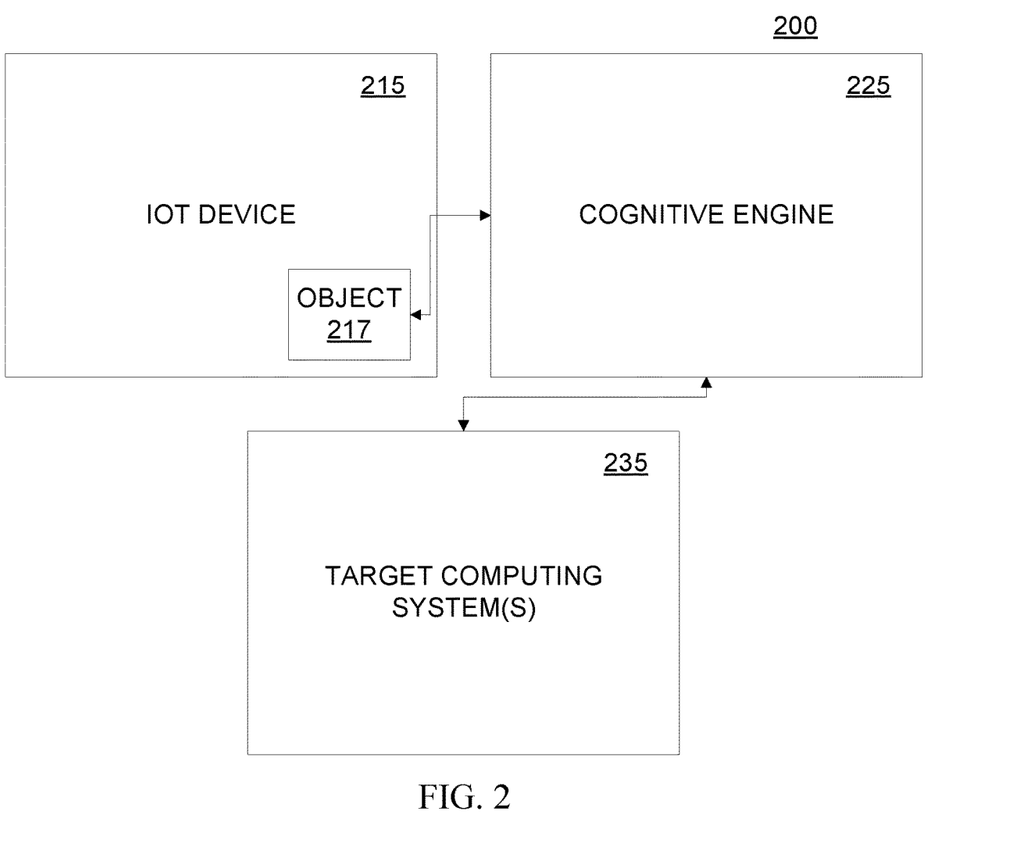
FIG. 2 is an illustration of certain aspects of an embodiment of the present invention.

FIG. 2 is a technical environment 200 into which various aspects of the method illustrated in FIG. 1 may be implemented. For clarity of illustration, only, certain aspects described in FIG. 1 are depicted as being included in certain modules of FIG. 2. For example, certain functionality is depicted in FIG. 2 as being accomplished by one or more programs in a cognitive engine 225, while other programs executed on an IoT device 215. This particular implementation and division of functionality is provided as a non-limiting example for clarity of illustration as the various programs can executed on varying computing resources across diverse computing environments.

Referring to FIG. 2, one or more programs executed by one or more computing resources in a technical environment 200 generate action plans based on a condition of an individual, as monitored by an IoT device 215, and execute the actions within a narrow timeframe, in order to prevent anticipated issues that have a probability of arising based on the condition of the individual. Thus, the technical environment 200 of FIG. 2 includes the aforementioned IoT device 215 in communication (over a public and/or private network, including the Internet) with a cognitive engine 225. In some embodiments of the present invention, the cognitive engine 225 may be internal to the IoT device 215. The cognitive engine 225 is communicatively coupled with one or more target computing systems 235 (a single system is pictured for simplicity).

In some embodiments of the present invention, based on passively obtaining health-related data from the IoT device 215, one or more programs comprising the cognitive engine 225 generate and execute one or more actions on the target computing systems 235. The one or more programs of the cognitive engine 225, in some embodiments of the present invention, access various applications (including a scheduling application) deployed on the one or more target computing systems 235, utilizing various communication methods, including but not limited to application programming interfaces (APIs), including representational state transfer (REST) APIs. Thus, the one or more programs may execute one or more tasks in the target computing system 235 by utilizing APIs to access applications deployed in these systems. As will be described herein, the one or more programs of the cognitive engine 225 may also query resources in the target computing systems 235 in order to generate an action plan before executing the actions contained in the plan.

In some embodiments of the present invention, the IoT device 215 that monitors a current condition of a user of the IoT device (FIG. 1, 110), is a wearable personal activity tracker. One or more programs of the IoT device 215 monitor the wearer as the IoT device is configured to detect, track and report data related to the current condition of the user, including the user's sleep patterns. To monitor the current condition, one or more programs executed by the IoT device 215 (optionally utilizing an object 217 provided by the cognitive engine 225) may monitor the sleep patterns of the user, including, but is not limited to, when the user goes to bed, how frequently the user wakes up, how long the user lies down or assumes a restful position, etc. Sleep patterns are only one example of types of data related to a current condition of a user that can be monitored by an IoT device 215 and utilized by a cognitive engine 225 in embodiments of the present invention. The functionality of the cognitive engine 225 is arguably most beneficial when analyzing health data related to dynamic conditions because so that one or more programs of the cognitive engine 225 cab automatically generate actions responsive to the dynamic conditions. For example, a given responsive action generate by the one or more programs may be relevant only when the one or more programs identify certain indicators in the data from the IoT device 215. Because sleep patterns are dynamic, data related to sleep patterns are used as an example is used herein to illustrate a current condition of an individual. However, in embodiments of the present invention, the IoT device 215 may collect data via passive monitoring the user of the device that may include, but is not limited to, data related to social and health habits of the user, vitals of the user, and/or data related to medical treatments of the user.

In some embodiments of the present invention, one or more programs of the cognitive engine 225 obtain the data related to a current condition of a user (e.g., sleep-related data) from the IoT device 215. The one or more programs may obtain the data either actively or passively, including by providing the IoT device program code with an object 217 that enables the IoT device to pass the data to the cognitive engine 225.

Upon obtaining the data (including concurrently and incrementally), the one or more programs of the cognitive engine 225 analyze the data to determine whether the data indicates that the current condition of the user indicates an issue (FIG. 1, 120). For example, if the data includes sleep-related data, the one or more programs of the cognitive engine 225 analyze the data to identify patterns and/or indicators that are suggestive of issues, including but not limited to, the user not having enough sleep, and/or the user not having sleep of an acceptable quality. Data analyzed by the one or more programs to identify these patterns and indicators may include, but are not limited to: time the user required to fall asleep, hours of sleep of the user per day/week/month/year, frequency and/or patterns of interruptions in sleep, periods in which the user remains in an Rapid Eye Movement (REM) sleep cycle versus in a non-REM sleep cycle.

One or more programs in the cognitive engine 225 may determine whether the user's current condition indicates that the user is experiencing an issue (FIG. 1, 120) by analyzing the collected data in view of data outlining healthful expectations for the user. The cognitive engine 225 itself may include a memory resource with wellness data that the one or more programs of the cognitive engine 225 can utilize to determine whether the collected data indicates an issue. The one or more programs may also utilize the connectivity of the cognitive engine 225 with one or more target computing systems 235 to access data external for the one or more programs to utilize in determining whether the collected data indicates an issue. The cognitive engine may obtain demographic data relevant to the user to determine that the user's activity represents a departure from expected (healthy) behavior. The cognitive engine 225 may obtain and utilize personal data identifying demographic information (e.g., from the IoT device 215 and/or an external computing resource) about the user in order to make determinations based on the collected data (e.g., because people benefit from different amounts of sleep at different ages, the one or more programs may obtain data relevant to healthy sleep patterns for the age group of the user). Based on the demographic information and the collected data from the IoT device 215, the one or more programs of the cognitive engine 225 determine that the collected data indicates an issue and identify the issue indicated. Returning to the sleep-related example, the one or more programs of the cognitive engine 225 detect if the user is not sleeping enough to maintain an expected level of wellness and/or if the quality of the sleep is too poor to maintain an expected level of wellness. In some embodiments of the present invention, the one or more programs determines that the current condition indicates an issue (FIG. 1, 120) when the identified issue persists over a period of time and/or over a defined threshold.

In some embodiments of the present invention, once the one or more programs determine that the current condition indicates an issue (FIG. 1, 120), the one or more programs alert designated individuals of the issue. For example, if the issue is that the user is sleep-deprived and he or she is expected to be a caregiver and that activity would be negatively impacted by the level of sleep deprivation that is the issue identified, the one or more programs of the cognitive engine 225 may access contact information of previously-designated individuals. The contact information may be accessible on a resource in the IoT device 215, the cognitive engine 225, and/or target computing systems 235. The one or more programs may also search social media profiles or other personal information on accessible computer systems to collect contact information and to determine which contacts are designated to receive notifications. The one or more programs of the cognitive engine 225 send an electronic alert (text, email, etc.) to designated contacts, requesting assistance. The one or more programs of the cognitive engine 225 may utilize resources and/or functionality, accessible of a target computer system 235 to generate the notifications. In the example of the sleep-deprived caregiver, the one or more programs may automatically contact a close relative to assist the user with this activity. In some embodiments of the present invention, the one or more programs include details describing the condition of the user in the notification.

In some embodiments of the present invention, rather than a user define contacts when specific issues are identified by the cognitive engine 225, the one or more programs access data related to contacts of the user (e.g., on a target computing system 235, on social media, via public search results) and determine which contacts should be contacted based on the issue. For example, in some embodiments of the present invention, the one or more programs of the cognitive engine 225 selects and notifies individuals based on profile information of the individuals, including but not limited to, age, physical condition, and/or availability. The one or more programs 225 determine, in some embodiments, that individuals with certain profiles are more appropriate to notify for certain issues. The appropriateness of an individual may depend on the activity that the individual will be asked to perform to mitigate the issue. For example, a user who is sleep deprived and would benefit from someone watching his or her small child for a few hours, the one or more programs may alert a close relative, such as a parent and in-law, with a request come over to the user's home. In the event that the user is suffering from a medical issue and needs transportation to a healthcare facility, the one or more programs may alert an individual with scheduling availability who holds a valid driver's license.

In some embodiments of the present invention, the one or more programs may determine who to notify based on the proximity of individuals with connections (e.g., social media connections, address book entries) to the user. Many IoT devices include location devices (e.g., global positioning system devices, triangulation devices), thus, the one or more programs of the cognitive engine 225 may obtain the location of the user from the IoT device and utilize the contact information to locate individuals references as contacts. These individuals may be located through their IoT devices, mobile phones, fitness trackers, and/or profile information on social media sites. The one or more programs alert the individuals within a given proximity of the user of the user's need for assistance.

One or more programs of the cognitive engine 225, based on determining that the current condition indicates an issue (FIG. 1, 120) may also determine that that the current condition of the user will negatively impact upcoming events that the user is committed to attend (FIG. 1, 140). The one or more programs of the cognitive engine 225 may discover the future commitments of the user by connecting to a calendar system, for example, on a target computing system 235. The appointments of the user may also be saved on the IoT device 215. By communicating over a private or public network (including the Internet) with a target computing system 235 or other external or internal resource(s) that includes the user's calendar, the one or more programs of the cognitive engine 225 identify one or more upcoming events within a given temporal period in which the user will participate (FIG. 1, 130) and one or more programs determine that the current condition of the user (i.e., the issue identified) will negatively impact at least one event of the more one or more upcoming events (FIG. 1, 130). The one or more programs may determine that the user's issue will negatively impact the one or more events within a given probability, based on the duration and/or severity of the issue, as determined by the one or more programs of the cognitive engine 225, based on (continuously) analyzing the data from the IoT device 215 (FIG. 1, 120).

In inter-connectivity of the cognitive engine 225 with the target computer systems 235 not only enables the cognitive engine 225 to access data that will be impacted by the condition of the user, but also enables the one or more programs of the cognitive engine 225 to take actions that will mitigate anticipated issues. Based on determining that the user's issue will negatively impact the one or more events, the one or more programs of the cognitive engine 225 generate at least one action that, when executed, will make a change to the at least one event that will mitigate the negative impact (FIG. 1, 150).

Returning to the scheduling example, the one or more programs of the cognitive engine 225 may determine that based on the level of sleep deprivation experienced by the user, the user will be unable to effectively lead a meeting he or she is scheduled to lead within a given time period of a poor night of sleep. Thus, the one or more programs of the cognitive engine 225 may determine that an action that would mitigate the perceived issue would be to cancel and/or reschedule the meeting. Based on the one or more programs generating this action (i.e., cancelling and/or rescheduling the meeting) (FIG. 1, 150), the one or more programs execute the action (FIG. 1, 160). Thus, in some embodiments of the present invention, the one or more programs may reschedule and/or cancel a scheduled meeting, based on the condition of the user including sleep deprivation that is anticipated to impact the scheduled meeting. By interacting with the scheduling system, the one or more programs may execute all the activities surrounding cancelling or rescheduling the meeting, including notifying all the attendees of the change. In some embodiments of the present invention, the one or more programs may alter details of a meeting to accommodate the user. For example, the one or more programs may distribute a call-in number for a formerly in-person meeting, so that the user can attend remotely.

In some embodiments of the present invention, rather than automatically implement actions to address perceived upcoming issues, the one or more programs of cognitive engine 225 may suggest actions to contacts of the user, as well as to the user, directly. Regarding the later, upon determining that a user is sleep-deprived, the one or more programs may determine, based on accessing the user's calendar (e.g., on a target computing system 235) that the user is sleep-deprived and does not have any scheduled appointments for a given period of time. The one or more programs may prompt the user to schedule a break for at least part of the period of time. In some embodiments of the present invention, the one or more programs may present the notification to the user through a GUI of the IoT device 215.

In some embodiments of the present invention, should the one or more programs observe a pattern of increased or persistent issues related to the condition of the user, the one or more programs may generate an escalated alert. An escalated alert may include notifying certain contacts (predefined or determined to be close to the user through public resources, such as social media), that the user is in need of a high level of assistance.

Referring now to FIG. 3, a schematic of an example of a computing node, which can be a cloud computing node 10. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove. In an embodiment of the present invention, the computing resources including the IoT device 215, the cognitive engine 225, and/or one or more of the target computer resources 235 can be understood as one or more cloud computing nodes 10 (FIG. 3) and if not examples of a cloud computing node 10, then one or more general computing nodes that include aspects of the cloud computing node 10.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 3, computer system/server 12 that can be utilized as cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples include, but are not limited to: microcode, device drivers, redundant processing units, external disk drive arrays, RAID systems, tape drives, and data archival storage systems, etc.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs). Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter). Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 4:
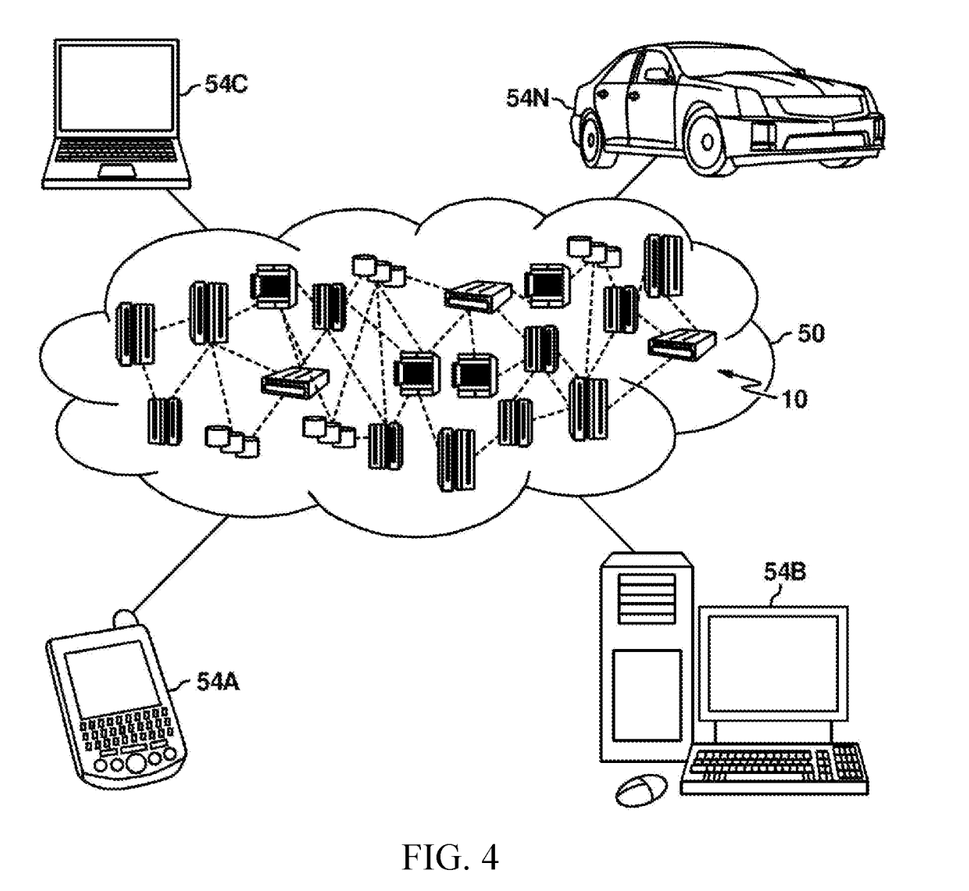
FIG. 4 depicts a cloud computing environment according to an embodiment of the present invention.

Referring now to FIG. 4, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 4 are intended to be illustrative only and that computing nodes 10 and cloud computing environment 50 can communicate with any type of computerized device over any type of network and/or network addressable connection (e.g., using a web browser).

Figure 5:
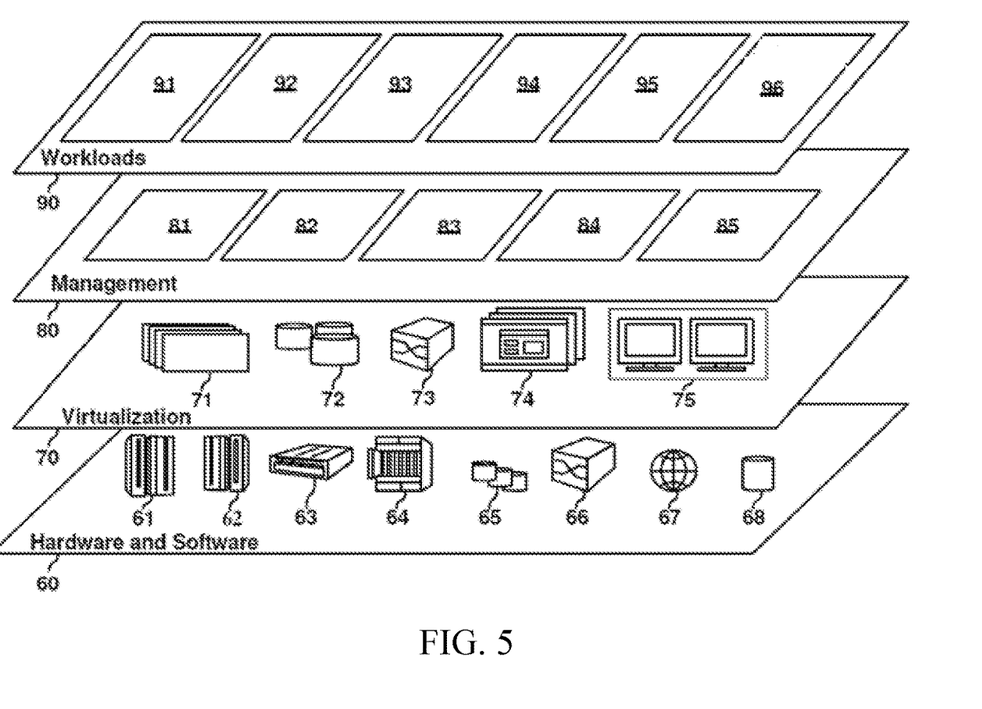
FIG. 5 depicts abstraction model layers according to an embodiment of the present invention.

Referring now to FIG. 5, a set of functional abstraction layers provided by cloud computing environment 50 (FIG. 4) is shown. It should be understood in advance that the components, layers, and functions shown in FIG. 5 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and interacting with various external systems to initiate actions to mitigate issues 96.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components and/or groups thereof.

The corresponding structures, materials, acts, and equivalents of all means or step plus function elements in the claims below, if any, are intended to include any structure, material, or act for performing the function in combination with other claimed elements as specifically claimed. The description of one or more embodiments has been presented for purposes of illustration and description, but is not intended to be exhaustive or limited to in the form disclosed. Many modifications and variations will be apparent to those of ordinary skill in the art. The embodiment was chosen and described in order to best explain various aspects and the practical application, and to enable others of ordinary skill in the art to understand various embodiments with various modifications as are suited to the particular use contemplated.

What is claimed is:

1. A computer-implemented method, comprising:

providing, by a cognitive engine comprising one or more processors, to an Internet of Things (IoT) device, an object, wherein the object enables the IoT device to pass data obtained by the IoT device to the cognitive engine, over a secure connection on a trusted network, wherein the IoT device automatically installs the object;

based on the IoT device automatically installing the object, continuously monitoring, by one or more processors, a current condition of a user of the IoT device, via the IoT device, wherein the continuously monitoring comprises utilizing the object provided by the cognitive engine to passively monitor the current condition by obtaining data from the IoT device, wherein the data comprises health indicators and sleep activity of the user;

identifying, by the one or more processors, over a given period of time, based on the continuously monitoring, wellness patterns of the user in the data;

obtaining, by the one or more processors, from a computing resource in the trusted network, demographic data comprising expected health patterns for a demographic relevant to the user;

generating, by the one or more processors, based on identifying the patterns and obtaining the demographic data, an electronic model representing an expected health condition of the user;

continuously analyzing, by the one or more processors, the continuously obtained data to identify deviations from the expected health condition of the user;

determining, by the one or more processors, at a given time, that the current condition indicates a given deviation from the expected health condition of the user;

identifying, by the one or more processors, one or more upcoming events, within a given temporal period, in which the user will participate, wherein the identifying comprises:

identifying, by the one or more processors, a computer resource of one or more target computer resources comprising a scheduling program, wherein the trusted network comprises the one or more target resources;

querying, by the one or more processors, over a network connection, the scheduling program, to obtain events relevant to the user; and analyzing, by the one or more processors, the events relevant to the user to identify the one or more upcoming events;

determining, by the one or more processors, that the current condition of the user will negatively impact at least one event of the more one or more upcoming events;

generating, by the one or more processors, at least one action comprising a change to the at least one event to mitigate the negative impact, wherein the at least one action is executed by interacting with one or more applications deployed on the one or more target computer resources, wherein the one or more target computer resources are accessible to the one or more processors via a network connection;

automatically executing, by the one or more processors, in real-time, the at least one action on the one or more target computer resources to implement the change in the one or more target computer systems in advance of the negatively impacted at least one event of the more one or more upcoming events, wherein the change comprises implementing a change to data in the scheduling program; and automatically notifying, by the one or more processors, a given contact of the user of the given deviation, wherein the given contact is one of one or more contacts stored in the IoT device as a trusted party, wherein the notifying is through an interface of a personal device of the contact, and wherein the given contact is notified based on being a contact of the one or more contacts in closest physical proximity to the user at the given time.

2. The computer-implemented method of claim 1, wherein implementing the change to data in the scheduling program comprises executing one or more tasks in the scheduling program.

3. The computer-implemented of claim 2, wherein the tasks are selected from the group consisting of: rescheduling the one or more upcoming events, cancelling the one or more upcoming events, alerting attendees of the one or more upcoming events to a change in the one or more upcoming events, and implementing a change to the one or more upcoming events.

4. The computer-implemented method of claim 1, wherein the IoT device is a wearable activity tracker.

5. The computer-implemented method of claim 1, wherein the continuously monitoring the current condition comprising the health indicators and the sleep activity of the user comprises collecting data selected from the group consisting of: heart rate information, biometric data, sleep information, and sleep pattern data.

6. The computer-implemented method of claim 5, the collected data further comprising motion data of the user.

\* \* \* \* \*